United States Patent [19]

Schieberl et al.

[11] Patent Number: 5,022,402
[45] Date of Patent: Jun. 11, 1991

[54] BLADDER DEVICE FOR MONITORING PULSE AND RESPIRATION RATE

[76] Inventors: Daniel L. Schieberl, 108 Eighth St., Santa Rosa, Calif. 95401; Greg Luzaich, 1555 Copperhill Pkwy., Santa Rosa, Calif. 95403

[21] Appl. No.: 445,181

[22] Filed: Dec. 4, 1989

[51] Int. Cl.⁵ .............................................. A61B 5/02
[52] U.S. Cl. .................................... 128/671; 128/721; 128/715; 128/689; 128/773
[58] Field of Search ............... 128/674, 671, 670, 675, 128/679, 684, 689, 691, 698, 701, 703, 713, 714, 715, 721, 691, 773

[56] References Cited

U.S. PATENT DOCUMENTS

| | | | |
|---|---|---|---|
| 2,194,809 | 5/1939 | Powell, Jr. | 128/721 |
| 3,572,317 | 10/1968 | Wade | 128/671 |
| 3,858,575 | 1/1975 | Rose | 128/773 |
| 4,619,270 | 10/1986 | Margolis et al. | 128/721 |
| 4,672,976 | 6/1987 | Kroll | 128/715 |
| 4,873,986 | 3/1989 | Wallace | 128/698 |
| 4,889,131 | 12/1989 | Salem et al. | 128/671 |

Primary Examiner—Stephen C. Pellegrino
Assistant Examiner—Robin R. Longo
Attorney, Agent, or Firm—Larry D. Johnson

[57] ABSTRACT

A medical monitoring device monitors the pulse and respiration rate of an infant, and transmits an alarm signal to a remote receiver when pulse and/or respiration rate irregularities are detected. The device incorporates an acoustic sensor (microphone) and pressure sensor adjacent a small gas or liquid-filled bag or bladder member. The bladder member and attached sensors are contained in a compact monitor housing which is positioned against the monitored infant's body, so that the bladder member directly contacts the body, and is preferably held in place by a small belt wrapped around the infant.

8 Claims, 2 Drawing Sheets

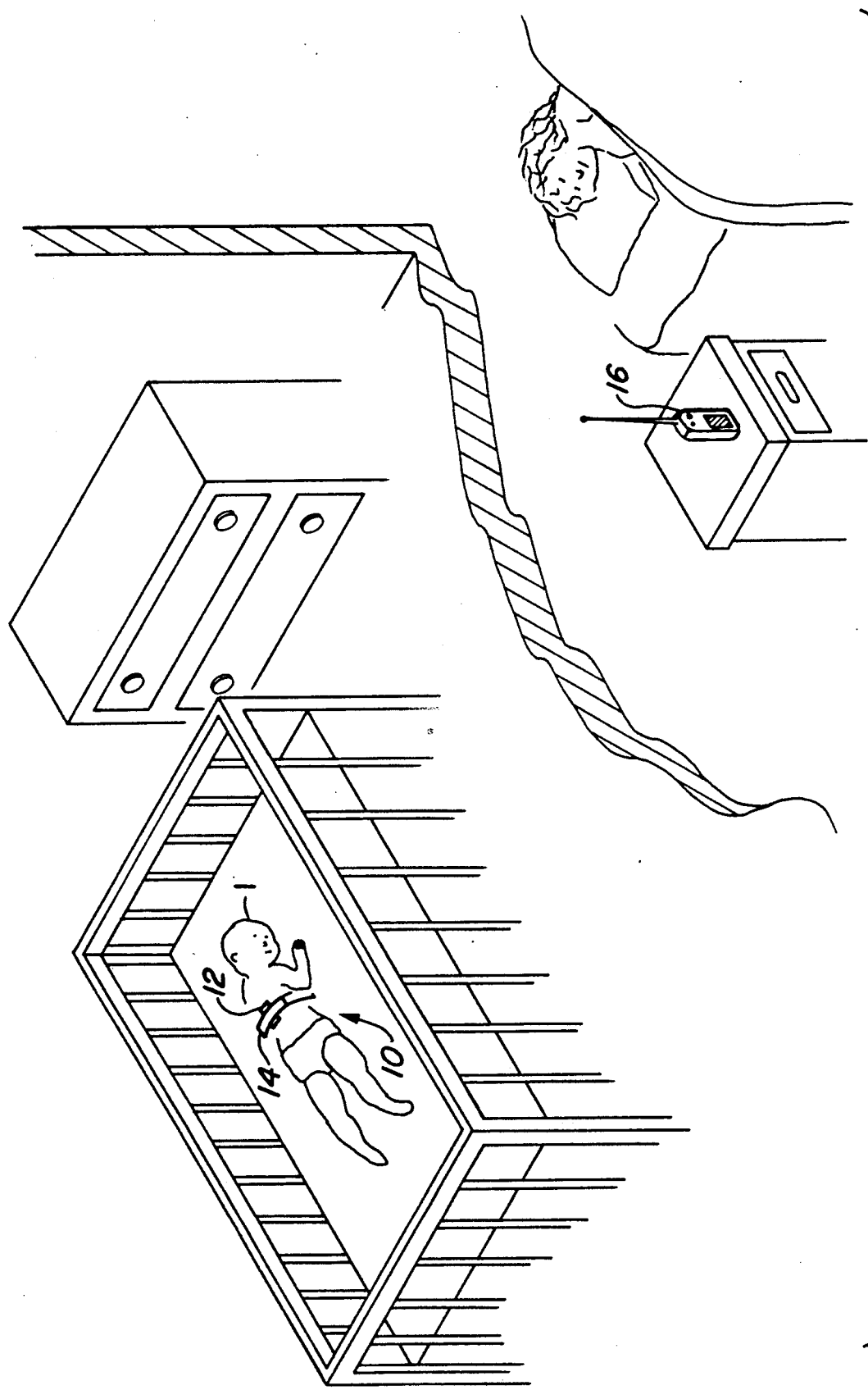
FIG._1

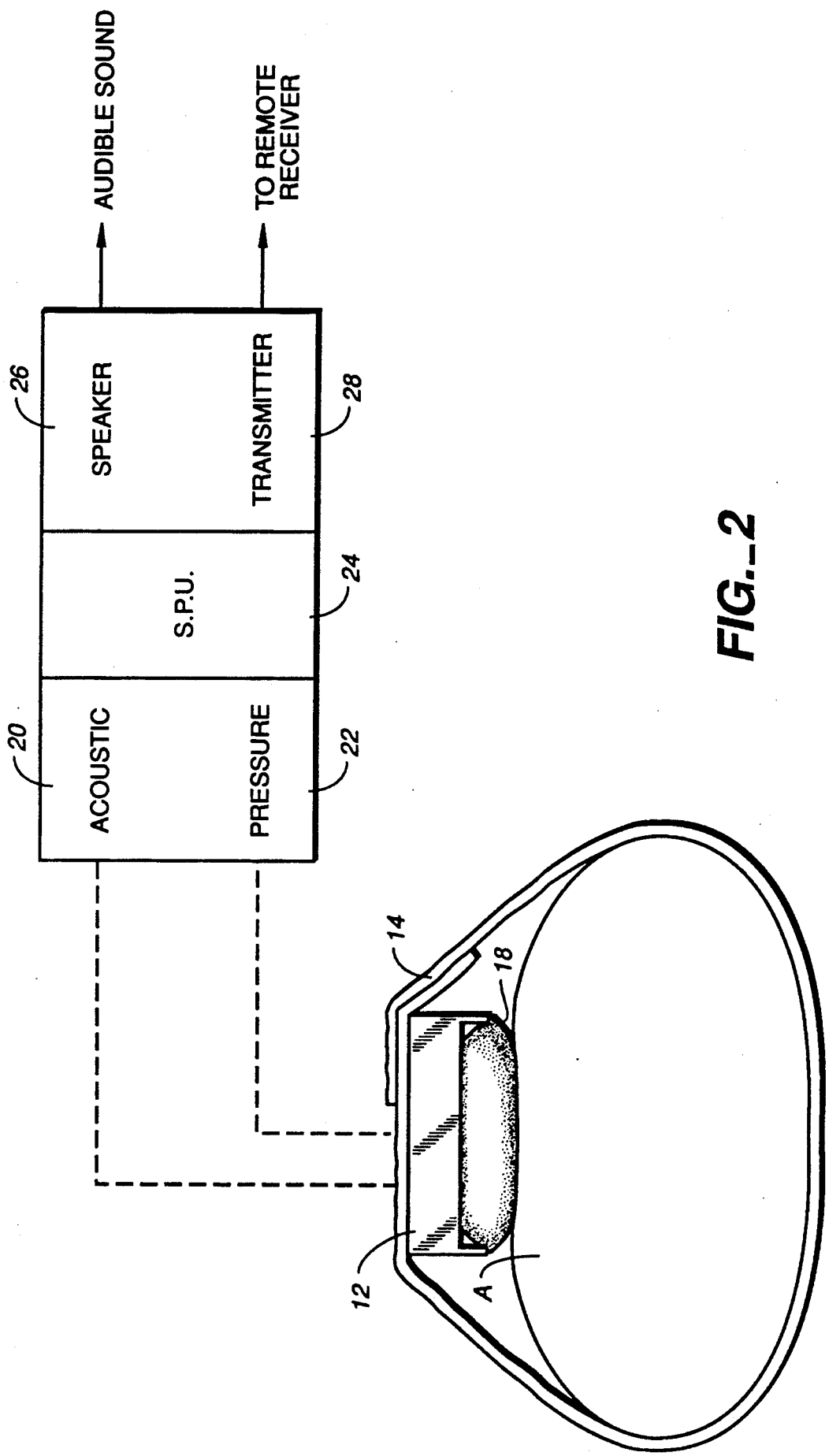
FIG._2

BLADDER DEVICE FOR MONITORING PULSE AND RESPIRATION RATE

BACKGROUND OF THE INVENTION

1. Field of the Invention

This invention relates generally to health care equipment and related diagnostic apparatus, and more specifically to an improved medical monitoring device for detecting pulse and respiration in an individual, and alerting a user to any irregularities.

2. Description of the Prior Art

Sudden Infant Death Syndrome (SIDS) is the number one killer of infants under the age of one year in the United States. Each year SIDS claims the lives of more than seven thousand infants in this country alone. To this date, there has been no cure discovered for this dreaded disease. SIDS can strike perfectly healthy infants which have exhibited no health abnormalities, thus making the diagnosis of SIDS very difficult. Currently, the only form of prevention is the use of expensive monitoring devices which sell for approximately three thousand dollars. The cost of these devices proves unaffordable for most families.

The rationale for development of an improved medical monitoring device stems from two criteria posed by the SIDS problem. The first is that if all infants were monitored between the ages of zero to twelve months, the number of deaths from SIDS might drop significantly. In order for this to be accomplished the second criteria must be met, that is, the device must be affordable to as many families as possible. Along with these two criteria, the guidelines for a suitable medical monitoring device include the following:

(a) the device must reliably monitor both the respiratory rate and the pulse rate of the infant;

(b) the device must be reliable and produce a minimum of false alarms while in use;

(c) the device must be small, have no wires attached to the infant, and may not disturb the infant while in use; and (d) the device must use radio signals to trigger an alarm device remotely located in another part of the house.

SUMMARY OF THE INVENTION

The medical monitoring device of this invention provides an inexpensive, compact, and unobtrusive system to reliably monitor the pulse and respiration rate of an infant, and to transmit an alarm signal to a remote receiver when pulse and/or respiration rate irregularities are detected. The device incorporates an acoustic sensor (microphone) and pressure sensor adjacent a small gas or liquid-filled bag or bladder member. The bladder member attached sensors are contained in a compact monitor case or housing which is positioned against the monitored infant's body, so that the bladder member directly contacts the body, preferably in a location where pulse and respiration can readily be sensed, e.g., the infant's abdomen or back. The monitor housing is preferably held in space in such a location by a small belt wrapped around the infant.

The monitor's acoustic sensor (microphone) is capable of direct sensing of the infant's heartbeat sounds, while the pressure sensor detects the change in pressure caused by the infant's periodic respiration. For example, the expansion of the infant's lungs and body during each inhalation acts to compress the bladder member against the monitor housing and belt, thereby creating an increase in the pressure of the contents by the pressure sensor.

Both the acoustic sensor and pressure sensor each deliver their respective signals to a signal processing unit, also contained in the monitor housing, which measures the time of receipt of each of these ongoing, repetitive signals. If the repetition of either signal is not received within a preselected time from the previously received signal (e.g., fourteen seconds), the signal processing unit delivers an alarm tone to an integral amplifier and alarm speaker (also contained in the monitor housing) to audibly alert the infant and/or any person in the immediate vicinity. In addition, the signal processing unit simultaneously activates an integral radio transmitter for transmission of a coded alarm signal to a remote receiver (e.g., located in the infant's parent's room), which in turn delivers an alarm tone to a separate amplifier and alarm speaker in the remote unit to audibly alert any person in that vicinity. Thus, within a split second of an alarm condition, the remote receiver receives a signal from the monitoring unit and emits an audible alarm to alert the parents of the infant's pending condition, thus giving the parents an ample amount of time to resuscitate the infant should it be necessary. In addition, the sound emitted by the self-contained monitor alarm speaker may be enough in itself to startle and revive the infant, The medical monitoring device of this invention has some exceptional design features. The device preferably uses state-of-the-art electronics to accurately monitor the pulse and respiratory rates of the infant with a high degree of reliability. The device functions without the use of wires or electrodes to the infant, and will run on battery power for approximately five weeks without battery replacement. The device preferably has built-in malfunction circuitry which automatically alerts the parents when the device is malfunctioning. The overall size of the preferred embodiment of the unit is approximately two inches by two inches by three-quarter inches. It is intended that every unit will be accompanied by a pamphlet which contains a set of instructions explaining what action can be taken to resuscitate the infant in the event of an emergency situation. At an approximate sales price of one hundred dollars, this will be a very affordable and marketable product which will make a significant contribution in the prevention of SIDS.

In addition to the monitor's uses with infants, the monitor realizes a tremendous potential in other markets. These markets include use by senior citizens, in veterinary applications, with military personnel, and for people with health problems.

BRIEF DESCRIPTION OF THE DRAWINGS

FIG. 1 is a pictorial view of the medical monitoring device of this invention in place as worn on an infant to be monitored, illustrating the monitor portion housing containing the bladder member, acoustic and pressure sensors, signal processing unit, monitor alarm speaker, and transmitter; the belt portion; and the remote portion containing the receiver and remote alarm speaker; and FIG. 2 is a schematic cross-sectional view of the monitor portion housing of the medical monitoring device of this invention as worn on an infant to be monitored, illustrating the monitor housing containing the bladder member, acoustic sensor, pressure sensor, signal processing unit, monitor alarm speaker, and transmitter, and held in place on the infant's body by the belt portion.

DETAILED DESCRIPTION OF A PREFERRED EMBODIMENT

FIG. 1 is a pictorial view of the medical monitoring device 10 of this invention in place as worn on an infant I to be monitored, illustrating the monitor portion housing 12 containing the bladder member, acoustic and pressure sensors, signal processing unit, monitor alarm speaker, and transmitter; the belt portion 14; and the remote portion 16 containing the receiver and remote alarm speaker. This view illustrates the preferred embodiment in which the sensors of the monitor detect pulse and/or respiration rate irregularities, and simultaneously activate an audible alarm both at the monitor location upon the infant, and at the remote location (e.g., a parent's room).

FIG. 2 is a schematic cross-sectional view of the monitor portion housing of the medical monitoring device of this invention as worn on the abdomen A of an infant to be monitored, illustrating the monitor housing 12 containing the bladder member 18, acoustic sensor 20, pressure sensor 22, signal processing unit 24, monitor alarm speaker 26, and transmitter 28, and held in place on the infant's body by the belt portion 14. Bladder member 18 is preferably filled with air to a nominal pressure e.g. +2 psi. It provides adequate contact area with the infant's body for receipt of the heartbeat acoustics, as well as reaction to the expansion of the infant's body during its inhalation. Accordingly, the unit should be placed on the body in a location where both heartbeat acoustics and respiratory expansion can be detected, as, for example, on the abdomen, back, or chest. Acoustic sensor 20 can be any standard microphone of sufficient sentivity and ouput. Pressure sensor 22 is preferably a semiconductor pressure transducer. Signal processing unit 24 utilizes well known electronic technology to time the repetitive signals from the sensors. Monitor alarm speaker 26 can be any compact speaker mechanism sufficient to emit an audible, and preferably startling, sound. Transmitter 28 can be any low-to-moderate power radio transmitter, and may even enable frequency selection between it and the receiver (coding, as with garage doors openers and the like) to prevent unwanted transmission/reception. Transmitter 28 may have an integral antenna, or may use an appropriate external antenna incorporated into belt portion 14.

While this invention has been described in connection with preferred embodiments thereof, it is obviopus that modifications and changes therein may be made by those skilled in the art to which it pertains without departing from the spirit and scope of the invention. For example, the monitor and receiver portions could be readily integrated into the complementary portions of a standard "baby monitor" device which transmit an infant's noises to a remote receiver, thereby greatly enhancing the usefulness of these common monitors.

Accordingly, the scope of this invention is to be limited only by the appended claims.

What is claimed as invention is:

1. A medical monitoring device for monitoring the pulse and respiration rate of an individual, said device comprising:

a bladder member having means conditioned for placement against and contact with the body of said individuals, said bladder member including attached acoustic sensor means for detection o the heartbeat sounds of said individual, and delivery of a pulse signal when such heartbeat sounds are detected, said bladder member further including attached pressure sensor means for detection of the bodily expansion during respiration by the indivdual, and delivery of a respiration signal when such bodily expansion is detected;

signal processing means for receiving said pulse signal delivered by said acoustic sensor and said respiration signal delivered by said pressure sensor, said signal processing means conditioned to time the repetitive receipt of each of said pulse signal and said respiration signal, said signal processing means further conditioned to deliver an alarm signal when either of said pulse signal or said respiration signal is not received within a predetermined time;

speaker means for generation of an audible alarm upon receipt of said alarm signal from said signal processing means;

transmitter means for transmission of a radio alarms signal upon receipt of said alarm from said signal processing means; and remote alarm means for receipt of said radio alarm signal from said transmitter means, and generation of a remote audible alarm upon such receipt.

2. The medical monitoring device of claim 1 wherein said acoustic sensor means comprises a microphone attached to said bladder member.

3. The medical monitoring device of claim 1 wherein said pressure sensor means comprises a semiconductor pressure transducer conditioned to detect pressure change in said bladder member.

4. The medical monitoring device of claim 1 wherein said bladder member comprises an air-filled bag.

5. The medical monitoring device of claim 1 wherein said transmitter means and said remote alarm means each include means to select the frequency of said radio alarm signal.

6. The medical monitoring device of claim 1 wherein said transmitter means includes an integral antenna.

7. The medical monitoring device of claim 1 wherein said device includes a belt portion for securing said bladder member against said individual's body, and said transmitter means includes an antenna incorporated into said belt portion;

8. The medical monitoring device of claim 1 further including housing means for containing said bladder member, said signal processing means, said speaker means, and said transmitter means.

* * * * *